United States Patent [19]
Walker

[11] 4,454,434
[45] Jun. 12, 1984

[54] CALIBRATION AND STATUS MONITOR COMPARATOR APPARATUS AND METHOD

[75] Inventor: Starnes E. Walker, Bartlesville, Okla.

[73] Assignee: Phillips Petroleum Company, Bartlesville, Okla.

[21] Appl. No.: 326,778

[22] Filed: Dec. 2, 1981

Related U.S. Application Data

[62] Division of Ser. No. 99,272, Dec. 3, 1979, Pat. No. 4,327,523.

[51] Int. Cl.³ .......................... H03K 9/06; H03K 5/26
[52] U.S. Cl. ..................................... 307/523; 307/273; 307/524; 328/141

[58] Field of Search ...................... 328/138, 140, 141; 307/522, 523, 524, 273

[56] References Cited

U.S. PATENT DOCUMENTS

| 3,099,800 | 7/1963 | Vinson et al. | 328/138 |
| 3,187,202 | 6/1965 | Case | 307/523 |
| 3,305,732 | 2/1967 | Grossman et al. | 307/524 |
| 3,539,827 | 11/1970 | Crowe | 307/522 |
| 4,021,794 | 5/1977 | Carlson | 328/138 |

Primary Examiner—John S. Heyman

[57] ABSTRACT

Comparator apparatus and method produce a signal representative of the relationship between two signals. In a further aspect, the comparator apparatus and method are used to provide a calibration and status monitor for a chromatographic analyzer.

3 Claims, 8 Drawing Figures

CALIBRATION AND STATUS MONITOR COMPARATOR APPARATUS AND METHOD

This application is a division of my copending application Ser. No. 099,272 filed Dec. 3, 1979, now U.S. Pat. No. 4,327,323.

The invention relates to a frequency comparator. In one aspect, the invention relates to a dielectric constant detector chromatographic analyzer employing a frequency comparator. In another aspect, the invention relates to a method for comprising frequencies. In yet another aspect, the inventory relates to a method of chromatographic analysis by determining dielectric constants.

The background, brief description, and detailed description of the present invention are set forth in terms of a frequency comparator which can be used in a dielectric constant detector chromatographic analyzer. However, the present invention provides a frequency comparator which can be used in applications other than in such chromatographic analyzers.

A chromatographic analyzer can be used to separate in time and individually detect the constituents of a sample to be analyzed. The chromatographic analyzer typically includes an analytical chromatographic column through which at least a carrier fluid can be passed continuously. The sample to be analyzed can be introduced into the carrier stream and thus carried through the column. The sample constituents are separated in time by being carried through the column at different velocities and eluted from the column at different times.

A detector can be used as part of the chromatographic analyzer to detect the separated constituents eluted from the column. The output signal from the detector is typically plotted as a function of time to produce what is known as a chromatogram. As each sample constituent is eluted from the column and detected, the detection of the constituent can, for example, result in a sharp increase in the detector output signal amplitude, which increase can appear as a spike or peak in the chromatogram.

Several detectors are available which can be used in liquid chromatography to provide an electrical signal representative of the concentration of sample constituents being eluted from a chromatographic column. Two widely used detectors are the ultraviolet absorption detector and the refractive index detector. The ultraviolet absorption detector is the more sensitive of the two, but is limited in application to substances that absorb ultraviolet radiation at the particular wavelength utilized. Not all substances exhibit sufficient absorption at ultraviolet wavelengths for the ultraviolet absorption detector to be useful. In contrast, the refractive index detector is a universal detector at least in the sense that all substances possess a refractive index which can in theory be detected unless the solvent and solute have identical refractive indexes. However, the relative difference between the refractive indexes for many solvent/solute systems is very small and for these systems it is difficult to obtain meaningful data utilizing a refractive index detector. Other liquid chromatography detectors such as electrical conductivity, fluorescence, radioactivity, and infrared absorption detectors are available but these detectors also have limited use.

Another detector relies upon detection of dielectric constants. The advantages of such a dielectric constant detector as a detector for liquid chromatography has been recognized. Like the refractive index detector, the dielectric constant detector is a universal detector since it responds to a change in a bulk property of the eluate from a chromatographic column. Use of dielectric constant detecting systems offers advantages over refractive index detecting systems because the relative differences in the dielectric constants of various substances are generally larger than the relative differences in refractive indexes. Refractive index detectors are capable of detecting refractive index changes as small as 0.1 ppm (parts per million). The dielectric constant detector of the present invention is capable of detecting dielectric constant changes of 0.5 ppm. Thus, the refractive index detector can be more sensitive than the dielectric constant detector for solvent/solute systems where the relative differences in the refractive indexes and the dielectric constants are approximately equal. Nevertheless, there are many practical solvent/solute systems where the dielectric constant detector has a definite advantage over the refractive index detector. The dielectric constant detector is particularly useful, for example, if the sample components have approximately equal dielectric constants which is, for example, the case for nonpolar hydrocarbons. By choosing a carrier that has a much higher dielectric constant, the sensitivity for each component is approximately equal and all the peaks are positive. This is rarely the case for a refractive index detector.

Typically a dielectric constant detector chromatographic analyzer utilizes a dielectric constant detector having a sample cell and a reference cell. Carrier fluid can be passed through the reference cell, while carrier fluid plus a sample constituent can be passed through the sample cell. A first electrical signal is produced which is representative of the fluid passing through a sample cell and a second electrical signal is produced representative of the fluid passing through the reference cell. The two electrical signals are compared to produce a third electrical signal representative of the sample constituent in the sample fluid.

It can be readily appreciated that accuracy requires that the relationship between the sample cell and the reference cell be known. The reference call and the sample cell can, for example, be balanced when carrier fluid is flowing through both the sample and the reference cells. Apparatus and method for balancing the cells in a simple straightforward way is therefore desirable.

It can also be appreciated that the dielectric constant detector can malfunction. For example, the plates of one or the other of the cells of the dielectric constant detector can become effectively shorted together resulting in an erroneous or distorted output. Apparatus and method for indicating such malfunctions is therefore desirable.

An object of this invention is a frequency comparator and method for producing a sensible signal representative of a frequency difference between a threshold frequency and an analysis frequency.

A further object of this invention is such an apparatus and method for producing a first sensible signal representative of a condition that the analysis frequency is substantially less than the threshold frequency, a second sensible signal representative of a condition that the analysis frequency is approaching, but less than, the threshold frequency, and a third sensible signal representative of a condition that the analysis frequency is equal to or greater than the threshold frequency.

Another object of this invention is such an apparatus and method wherein the threshold frequency is selectable from a group of at least two frequencies.

Another object is such an apparatus having high input impedance and high sensitivity to frequency changes.

Yet another object of this invention is apparatus and method for dielectric constant chromatographic analysis comprising such a comparator.

Other objects and advantages of this invention will be clear to one skilled in the art from the following disclosure and the claims.

Broadly, the invention comprises apparatus and method for dielectric constant chromatographic analysis comprising column means for chromatographically separating sample constituents to produce an eluate stream, means for passing a first carrier fluid stream to the column means, means for injecting sample constituents into the first carrier fluid stream being passed to the column means, dielectric constant detector means including sample cell means having a first capacitance representative of a fluid passing therethrough and reference cell means having a second capacitance repesentative of a fluid passing therethrough, mean for passing the eluate stream through the sample cell means, means for passing a second carrier fluid stream through the reference cell means, first oscillator means comprising said sample cell means for producing a first frequency representative of the first capacitance, second oscillator means comprising said reference cell means for producing a second frequency representative of the second capacitance, means for combining the first frequency and the second frequency to produce an analysis frequency representative of the difference between the first frequency and the second frequency, and comparator means for producing a sensible signal representative of a difference between a threshold frequency and the analysis frequency.

In another aspect the invention comprises comparator apparatus and method for producing a sensible signal representative of a difference between a threshold frequency and an analysis frequency, the invention comprising pulse generating means having an analysis frequency input, a timing circuit input, and a pulse output, and operable for producing a pulse at the pulse output responsive to an edge of an input pulse at the analysis frequency input, the pulse having a duration determined by a pulse width signal appearing at the timing circuit input, analysis frequency means for producing an analysis frequency, first means for electrically connecting the analysis frequency means to the analysis frequency input of the pulse generating means, timing circuit means for determining a threshold frequency and for producing a pulse width signal output responsive to an edge of an input pulse at the analysis frequency input, second means for electrically connecting the timing circuit means output to the timing circuit input of the pulse generating means, and means for producing a sensible signal representative of the difference between the threshold frequency and the analysis frequency.

Figure 4:
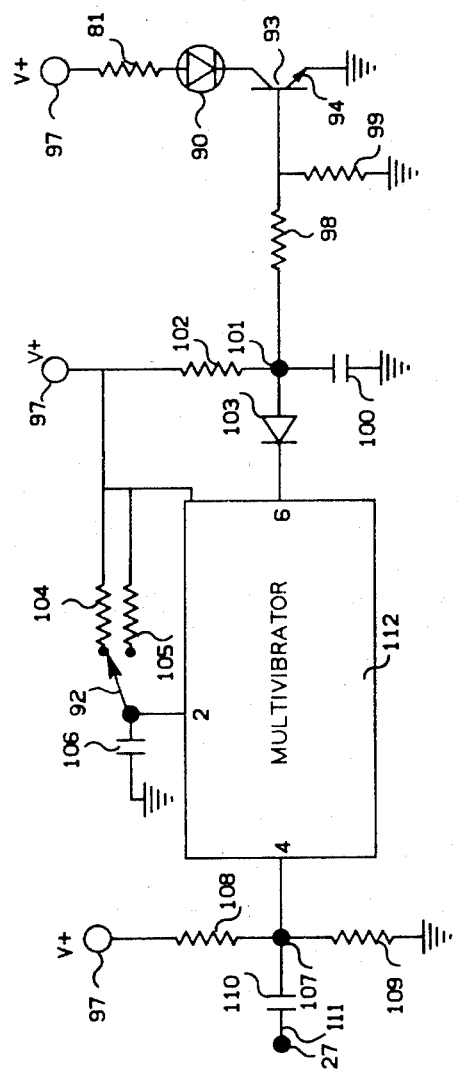
FIG. 4 is a schematic representation of the circuitry of the comparator 29 shown in FIG. 1.
Figure 5A:
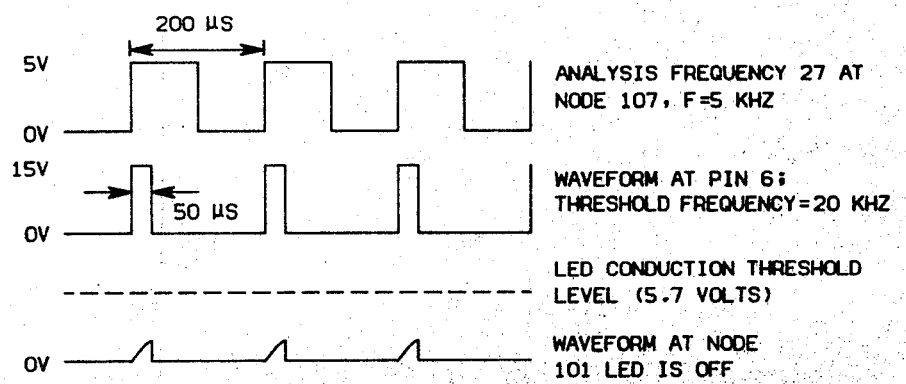
Figure 5B:
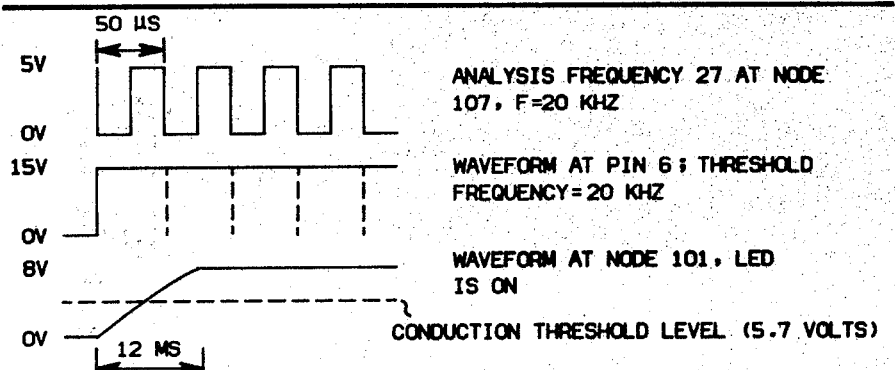
Figure 5C:
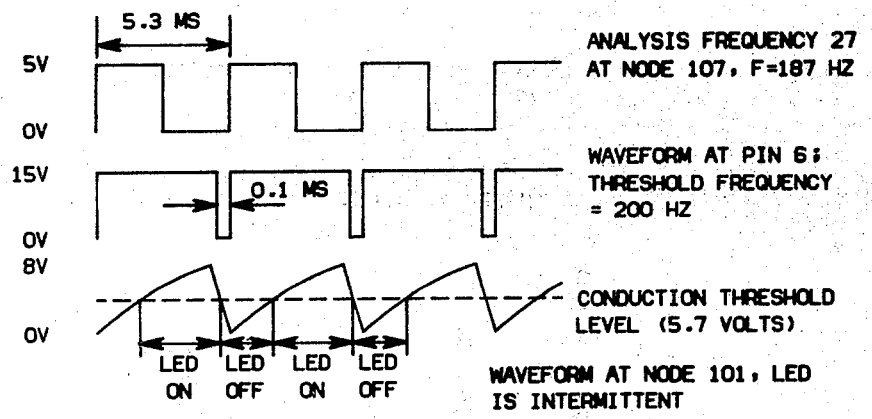
Figure 6:
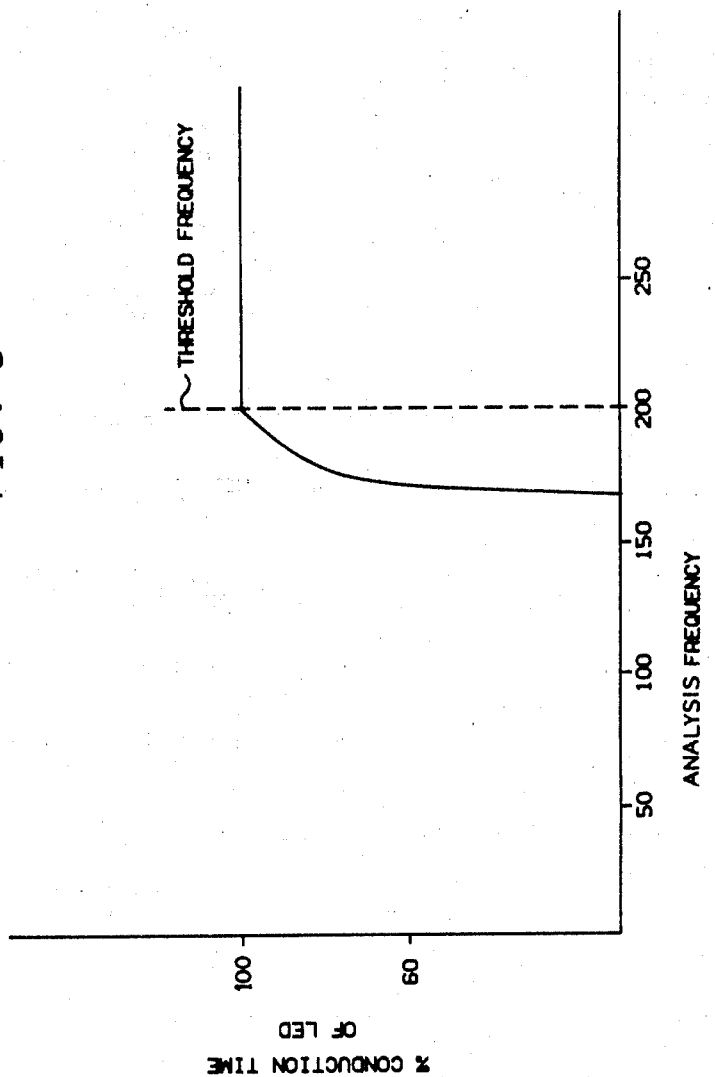

FIGS. 5A–5C show voltage wave forms at various points in the apparatus of FIG. 4 to illustrate circuit operation when an analysis frequency is below a threshold frequency, equal to a threshold frequency, and approaching a threshold frequency; and FIG. 6 shows a graph of the percent conduction of the output transistor versus input frequency to illustrate LED brilliance as a function of the relationship between the analysis frequency and a threshold frequency.

In accordance with one aspect of the present invention, method and apparatus is provided whereby a dielectric constant detector is utilized to provide an output which is representative of the concentration of sample constitutents of a sample being passed through the sample cell means of the dielectric constant detector means. The reference cell means and sample cell means of the dielectric constant detector means have first and second plates respectively. The distance separating the first and second plates of either the reference cell or the sample cell or both the reference cell and the sample cell is not a structurally fixed constant. The first and second plates which are separated by a nonconstant distance can be translated wth respect to each other in order to substantially match the capacitance of the sample cell and the capacitance of the reference cell when the same fluid is flowing through both the sample cell and reference cell. A method for matching the capacitance is described below.

Once the capacitance of the sample cell and reference cell have been substantially matched, a carrier fluid containing sample constituents of the sample is provided to the sample cell. At the same time carrier fluid only is provided to the reference cell. Electronic circuitry associated with the sample cell means provides an output signal having a frequency which is a function of the capacitance of the sample cell when the carrier fluid plus sample constituents is flowing through the sample cell. Electronic circuitry associated with the reference cell means also provides an output signal which has a frequency which is a function of the capacitance of the reference cell means when only the carrier fluid is passing through the reference cell means. The two output signals are mixed to provide an analysis frequency (difference frequency) and the analysis frequency is converted to a voltage to provide an electrical signal which is representative of the concentration of the particular sample constituent which is passing through the dielectric constant detector means.

In accordance with the present invention a frequency comparator is combined with the dielectric constant detector chromatographic analyzer. The comparator is preferably selectably operable to at least a first position and a second position. In the first position, the comparator functions to provide a calibration signal, and to set the base line operation of the dielectric constant detector means. In the second position, the comparator functions to provide an malfunction indication during operation of the dielectric constant detector.

Although the invention is described in terms of use of the frequency comparator in a dielectric constant detector of a specific chromatographic analyzer system, the invention is applicable to other uses. The dielectric constant detector means can also be used in applications other than chromatography. It is also noted that the invention is described in terms of a specific mechanical configuration for the dielectric constant detector. However, the invention is not limited to the specific configuration illustrated, but is rather applicable to any mechanical configuration which accomplishes the purpose of the present invention.

Figure 1:
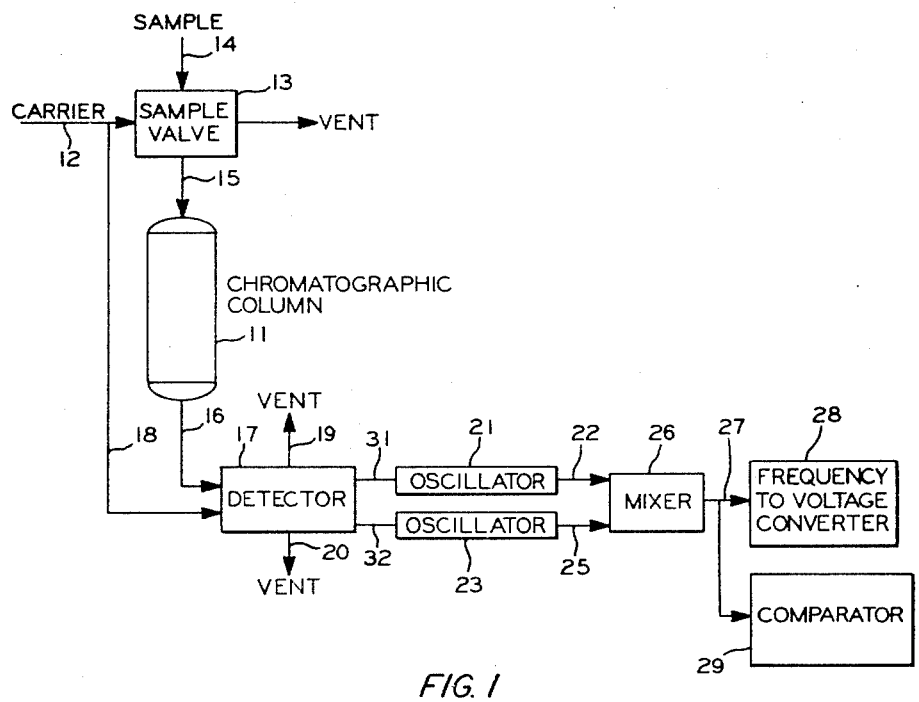
FIG. 1 is a block diagram of a dielectric constant chromatographic analyzer in accordance with the present invention.

In referring now to the drawing of FIG. 1, there is illustrated a chromatographic column 11. A sample of a fluid to be analyzed is delivered to sample valve 13 through conduit means 14. Conduit means 15 extends between sample valve 13 and the inlet of chromatographic column 11. Conduit means 16 extends between the outlet of chromatographic column 11 and the sample inlet of the dielectric constant detector 17. Carrier fluid is passed through the reference portion of the dielectric constant detector 17 by being introduced into the reference inlet of the dielectric constant detector 17 through conduit means 18 which is in fluid communication with conduit means 12. Carrier fluid flows through sample valve 13, chromatographic column 11, and conduit means 16 to the sample inlet of the dielectric constant detector 17. At the beginning of a chromatographic analysis, sample valve 13 is actuated to introduce a predetermined volume of sample into the carrier fluid flowing through chromatographic column 11. The constituents of the sample are eluted in sequence and flow as an eluate stream from the chromatographic column 11 through conduit means 16 to the sample cell of the dielectric constant detector 17. An electrical conductor 31 electrically connects one plate of the sample cell to the oscillator 21. An electrical conductor 32 electrically connects one plate of the reference cell to the oscillator 23. The sample cell of the dielectric constant detector 17 in conjunction with the oscillator 21 establishes an output signal 22 which has a first frequency which is representative of the capacitance of the sample cell when a particular constituent of the sample is passing through the sample cell. In like manner, the reference cell of the dielectric constant detector 17 in conjunction with the oscillator 23 provides an output signal 25 which has a second frequency which is representative of the capacitance of the reference cell when only carrier fluid is passing through the reference cell. Signal 22 is provided from the oscillator 21 as an input signal to the mixer 26. Signal 25 is provided from the oscillator 23 as an input to the mixer 26. Signals 22 and 25 are combined in the mixer 26 to provide an analysis frequency 27 which is representative of the difference frequency between the first frequency 22 and the second frequency 25. Analysis frequency 27 is provided from the mixer 26 as an input to the frequency-to-voltage converter 28. Analysis frequency 27 is converted from an oscillating signal to a DC voltage by the frequency-to-voltage converter 28 and the DC voltage will be representative of the concentration of the particular sample constituent passing through the sample cell. Analysis signal 27 is also supplied as an input to the comparator 29, whose circuitry and operation is described in more detail below.

Figure 2:
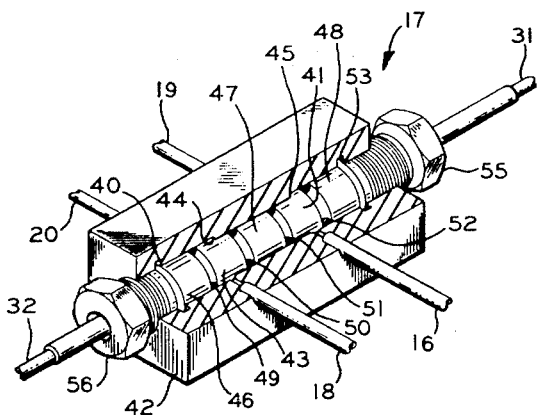
FIG. 2 is a detailed illustration of the dielectric constant detector means 17 shown in FIG. 1.

The dielectric constant detector 17 is more fully illustrated in FIG. 2. Referring now to FIG. 2, the sample cell with the dielectric constant detector 17 is formed by the center plate 41 and the outer plate 42. The reference cell is formed by the center plate 43 and the outer plate 42. All of the plates are preferably formed from stainless steel. The outer plate 42. which is common to both the sample cell and the reference cell, is preferably machined in the form of a prism having a substantially square transverse cross section. An opening extends therethrough for the length of the prism. The opening extending through the center portion of the prism forms first, second, and third serially contiguously connected cylindrical openings. The first cylindrical opening extends from the edge of the groove 40 which is adjacent the spacer 46 to a circular line 44 which lies in a plane which is at least substantially perpendicular to the longitudinal axis of the opening, the plane extending through the longitudinal mid-region of center plate 43. In the illustrated embodiment line 44 is formed by an annular shoulder. The second cylindrical opening extends from the line 44 to a circular line 45 which lies in a plane which is at least substantially perpendicular to the longitudinal axis of the opening, the plane extending through the longitudinal mid region of center plate 41. In the illustrated embodiment line 45 is formed by an annular shoulder. The third cylindrical opening extends from the line 45 to the edge of the groove 53 which is adjacent the spacer 48. The diameter of the first and third cylindrical openings are preferably substantially equal. The diameter of the second cylindrical opening is less than the diameter of the first and third cylindrical openings. The center plates 41 and 43 do not touch the outer plate 42 at any point. The center plates 41 and 43 are cylindrical in form and are electrically isolated by the spacers 46, 47, and 48 which are preferably formed from KEL-F, manufactured by Union Carbide. The O-rings 49 through 52, which are preferably Teflon, provide means for sealing the sample and reference cells to prevent leakage of fluid out of the sample and reference cells. The O-rings 49 through 52 also provide means for centering the center plates 41 and 43 with respect to the outer plate 42. The entire assembly consisting of the center plates 41 and 43, the spacers 46, 47, and 48 and the O-rings 49 through 52 is held in place by the end caps 55 and 56 which are coupled by means of threads to the outer plate 42. The end caps 55 and 56 also provide a means for longitudinally moving the center plates 41 and 43 with respect to the outer plate 42.

The electrical conductor 32 is electrically connected to the center plate 43 and is electrically isolated from the outer plate 42. The electrical conductor 31 is electrically connected to the center plate 41 and is electrically isolated from the outer plate 42. The outer plate 42 is electrically connected to ground.

The outer plate 42 and the center plate 41 form concentric cylindrical plates. Solute plus carrier is provided from the chromatographic column 11 through conduit means 16 to the space between the concentric cylindrical plates. All conduits are preferably 1/16-inch outside diameter × 0.010-inch inside diameter stainless steel tubing. The volume of the fluid which may be contained in the sample cell is determined by the position of the center plate 41 with respect to the outer plate 42. As has been previously noted, the second cylindrical opening in the outer plate 42 which extends into the sample cell has a smaller diameter than the first cylindrical opening in the outer plate 42 which also extends into the sample cell. Longitudinal movement of the center plate 41 with respect to the outer plate 42 will thus change plate surface area to a separation distance ratio, and hence the volume of fluid which can be contained in the simple cell. The product of the dielectric constant of the fluid passing through the cell and the ratio of the plate surface area to separation distance in the sample cell determines the nominal capacitance of the sample cell and by longitudinal movement of the center plate 41 with respect to outer plate 42, the capacitance of the sample cell can thus be adjusted. A method for adjusting the capacitance of the plates to balance the sample cell and the reference cell is described below.

In like manner, carrier fluid is provided through conduit means 18 to the reference cell. The center plate 43 can be moved longitudinally along the common axis with respect to the outer plate 42 so as to adjust the capacitance of the reference cell in the same manner as previously described for the sample cell.

Movement of the center plate 41 and the center plate 43 relative to outer plate 42 is accomplished by simultaneously turning the end caps 55 and 56. Preferably, for purposes of adjustment only, carrier fluid only is provided to both the sample cell and the reference cell. The end caps 55 and 56 are then simultaneously turned so as to substantially match the capacitance of the sample cell and the capacitance of the reference cell when the same fluid is flowing through both cells.

With nonadjustable cells, the best match generally obtainable is about 5 percent. That is to say, one cell will have about 5 percent more capacitance than the other cell. With the adjustable cells as herein described, the capacitance can be matched to 1/50th of 1 percent which results in an improvement of 250:1 over nonadjustable cells.

It is again noted that the present invention is applicable to any dielectric constant detector having any mechanical configuration of the plates of the sample and reference cells. Thus, parallel plate configurations or other desired plate configurations can be utilized if desired.

It is also noted that even though it is presently preferred to be able to vary the volume of fluid in both the sample and reference cells, it is only necessary that means be provided for varying the volume of fluid which can be contained in only one of the cells. Thus, the capacitance of one of the cells can be changed to match the capacitance of a cell which does not have means for adjusting the volume of fluid which can be contained in the cell.

Figure 3:
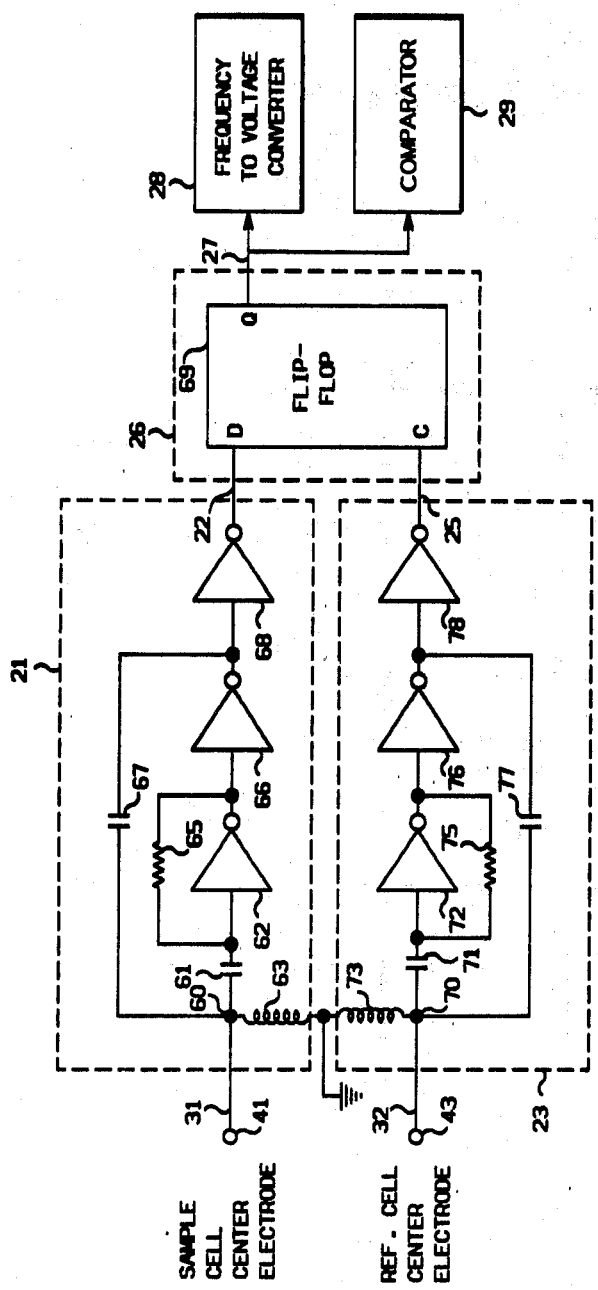
FIG. 3 is a schematic representation of the circuitry shown in FIG. 1 exclusive of the circuitry of comparator 29.

The oscillators 21 and 23 together with the mixer 26 and the frequency-to-voltage converter 28 illustrated in FIG. 1 are more fully illustrated in FIG. 3. Referring now to FIG. 3, the center plate 41 of the sample cell is electrically connected to node 60. The inductor 63 is electrically connected between node 60 and electrical ground. Node 60 and the input of the inverter 62 are electrically connected through the capacitor 61. The output of the inverter 62 is fed back to the input of the inverter 62 through resistor 65. The output of the inverter 62 is also electrically connected to the input of the inverter 66. The output of the inverter 66 is fed back to node 60 through capacitor 67. The output of the inverter 66 is also provided as an input to the inverter 68. The output of the inverter 68 forms signal 22 which has a frequency representative of the capacitance of the sample cell of the dielectric constant detector 17. Signal 22 is provided to the D input of the flipflop 69 which forms the mixer 26 illustrated in FIG. 1.

The center plate 43 of the sample cell is electrically connected to node 70. The inductor 73 is electrically connected between node 70 and electrical ground. Node 70 and the input of the inverter 72 are electrically connected through the capacitor 71. The output of the inverter 72 is fed back to the input of the inverter 72 through resistor 75. The output of the inverter 72 is also electrically connected to the input of the inverter 76. The output of the inverter 76 is fed back to node 70 through capacitor 77. The output of the inverter 76 is also provided as an input to the inverter 78. The output of the inverter 78 forms signal 25 which has a frequency representative of the capacitance of the reference cell of the dielectric constant detector 17. Signal 25 is provided to the C input of the flipflop 69 which forms the mixer 26 illustrated in FIG. 1.

The frequency of the output signal 22 from the sample oscillator 21 is determined primarily by the value of the inductor 63 and the capacitance of the sample cell of the dielectric constant detector 17. In like manner, the frequency of the output signal 25 from the reference oscillator 23 will be determined primarily by the value of inductor 73 and the capacitance of the reference cell of the dielectric constant detector 17. The values of inductors 63 and 73 are preferably substantially equal. Thus, the difference in the frequencies of signals 22 and 25 will be determined substantially solely by the difference between the capacitance of the reference cell and the capacitance of the sample cell. The difference between the capacitance of the reference cell and the capacitance of the sample cell is determined by the dielectric constant of the component of the sample which together with the carrier fluid is flowing through the sample cell of the dielectric constant detector. Thus, the difference in the frequencies of signals 22 and 25 will be a function of the dielectric constant of the component of the sample which together with the carrier fluid is flowing through the sample cell of the dielectric constant detector.

The flipflop 69 acts as a mixer. Thus, the Q output which is representative as signal 27 will be substantially equal to the difference in the frequencies of signals 22 and 25. Signal 27 is provided from the Q output of the flipflop 69 to the frequency-to-voltage converter 28 which can be, for example, a Model 453 J, K, or L obtainable from Analog Devices, Norwood, Mass. Signal 27 is converted from a AC signal to a DC voltage by the frequency-to-voltage converter 28 and the DC voltage will be proportional to the concentration of a constituent of the sample which is flowing through the sample cell of the dielectric constant detector 17.

Referring now to FIG. 4 in detail, reference numeral 29 refers generally to a frequency comparator in accordance with the present invention. Reference numeral 27 designates generally a signal source which is connected to a first lead of an input capacitor 110 by electrical connection means 111. A second lead of capacitor 110 is tied at node 107 to a first resistor 108, which resistor has a second lead tied to a voltage source, for example to a +15 volt power supply 97. The second lead of capacitor 110 is also tied to a first lead of second resistor 109, having a second lead tied to ground. The second lead of capacitor 110 is also tied to input pin 4 of monostable multivibrator 112.

Means 112 provides the function of a dual, retriggerable, resettable, monostable multivibrator. Means 112 is operable for producing an accurate output pulse at output terminal 6 over a wide range of pulse widths, the duration and accuracy of which are determined by external timing components electrically connected to input terminal 2 of means 112. In the illustrated embodiment, the external timing components comprise switch 92, capacitor 106, and a plurality of resistors, represented in the illustrated embodiment by the resistors 104 and 105. In a preferred embodiment means 112 is a Motorola Monostable Multivibrator Model MC 14528, available from Hamilton Avnet Electronics, Dallas, TX 75240. The pulse width timing terminal 2 (timing circuit input) of monostable multivibrator 112 is tied to a first lead of capacitor 106. The second lead of capacitor 106 is tied to ground. The pulse width timing terminal 2 is also tied to the common terminal of switch 92. The output terminal of switch 92 is selectably tied to a first lead of resistor 104 having a second lead tied to a voltage source 97 or to a first lead of resistor 105 having a second lead tied to voltage source 97.

The output terminal 6 of monostable multivibrator integrated circuit 112 is tied to the cathode of diode 103. The anode of diode 103 is tied to node 101. Node 101 is also tied to a first lead of resistor 102, having a second lead tied to voltage source 97. Node 101 is also tied to a first lead of capacitor 100 and to a first lead of resistor 98. The second lead of capacitor 100 is tied to ground. The second lead of resistor 98 is tied to the base of NPN transistor 93 and to a first lead of resistor 99. The second lead of resistor 99 and the emitter 94 of NPN transistor 93 are tied to ground. The collector of transistor 93 is tied to the cathode of light emitting diode (LED) 90. The anode of light emitting diode (LED) 90 is tied to a first lead of resistor 81 having a second lead tied to a voltage source 97.

The input circuit of monostable multivibrator 112 comprises capacitor 110 and a voltage divider network comprising resistor 108 and resistor 109. The analysis frequency signal from mixer 26 is coupled through capacitor 110 to the input pin 4 of monostable multivibrator means 112. For each positive going edge of the analysis frequency waveform, monostable multivibrator means 112 emits a pulse at output terminal 6. The pulse at output terminal 6 has a duration determined by the timing circuit comprising resistors 104 and 105, capacitor 106, and toggle switch 92.

In the illustrated embodiment, the timing circuit means for producing a pulse width signal output comprises, as indicated, capacitor 106, switch 92, resistors 104 and 105 and voltage source 97. When a positive going edge appears at input terminal 4 of means 112, capacitor 106 starts charging from voltage source 97 through a selectable one of resistors 104 and 105. As indicated, for each positive going edge of the analysis frequency waveform means 112 emits an output pulse at terminal 6. The output pulse at terminal 6 remains at a logic high until capacitor 106 is charged to a retrigger voltage level at which time the output pulse at terminal 6 of means 112 is reset to a logic low. The time required for capacitor 106 to reach this level is the reset time of the timing circuit. If the pulse width of the timing circuit is shorter than the period of the analysis frequency appearing at input terminal 4, then the output at terminal 6 will cycle between a logic high and a logic low during each cycle of the analysis frequency as shown in FIG. 5A. If the pulse width of the timing circuit is less than but close to the period of the analysis frequency, then the proportion of time the output at terminal 6 is at a logic low decreases as shown in FIG. 5C. When the pulse width is equal to or greater than the period of the analysis frequency, then the output at pin 6 effectively remains continuously at a logic high as shown in FIG. 5B. Thus, the output signal at pin 6 is representative of the relationship between the pulse width determined by timing circuit components and the period of the analysis frequency. The timing circuit reset time can be converted to a threshold by the equation $$f=(1/t)$$

where t is the reset time and f is the frequency of a signal having a period equal to t. Hence, it can be readily seen that the effect of means 112 is that the signal appearing at pin 6 is representative of the relationship between the analysis frequency and a selectable threshold frequency.

For example, suppose now that the threshold frequency is set at 20 kHz (t=50 microseconds) by selecting a value of 0.1 microfarad for capacitor 106 and a value of 920 ohms for resistor 105. For illustration purposes, suppose further that an analysis frequency of 5 kHz is coupled to node 107 through capacitor 110. Then, for each positive going edge of the signal source waveform shown in FIG. 5A, integrated circuit 112 emits a 50 microsecond pulse at output terminal 6. This pulse at pin 6 back biases diode 103 and thus allows capacitor 100 to charge towards 8 volts with a time constant determined by capacitor 100 and resistors 102, 98 and 99. For example, where the threshold voltage for conduction of NPN transistor 93 is, for example, 5.7 volts at the node 101, then in order for 5.7 volts to be reached, diode 103 must be back biased for approximately 11.8 milliseconds as determined from the equation $e_o = E(1 - e^{-t/RC})$, where $e_o$ is the instantaneous voltage across filter capacitor 100, E is the voltage that junction 101 would achieve if diode 103 remained back biased for a long period of time, and R is the resistance seen by capacitor 100. During the 50 microsecond period that diode 103 is back biased, $e_o$ attains a value of approximately 0.1 volt as determined from the above equation for $e_o$. Since the voltage at junction 101 does not attain a value sufficient to cause transistor 93 to conduct the light emitting diode remains off for an analysis frequency of 5 kHz and a threshold frequency of 20 kHz.

To further illustrate the operation of FIG. 4, suppose now that the threshold frequency is set at 20 kHz (t=50 microseconds) as before, but that an analysis frequency of 20 kHz is coupled to input junction 107. As shown in FIG. 5B, the wave form at terminal 6 of monostable multivibrator 112 goes positive when the leading edge of the 20 kHz first frequency appears at input terminal 2 and remains at approximately 15 volts positive continuously thereafter since the analysis frequency is equal to the threshold frequency. This voltage back biases diode 103 enabling capacitor 100 to charge producing the waveform at node 101 shown in FIG. 5B. Since the voltage appearing at node 101 exceeds 5.7 volts, the transistor 93 conducts and the light emitting diode 90 is on continuously.

To further illustrate the operation of the circuit of FIG. 4 suppose now that the analysis frequency at point 107 is for example 187 Hz (t=5.3 milliseconds) and that the threshold frequency set by the timing circuit at pin 2 is 200 Hz. As shown in FIG. 5C, this combination of analysis frequency and threshold frequency allows capacitor 100 to charge to an excess of 5.7 volts at node 101, but also to discharge to below 5.7 volts for each cycle of the analysis frequency at node 107. This results in allowing NPN transistor 93 to conduct for an interval during each analysis frequency cycle resulting in a rapidly flickering or, in effect, less brilliant visual appearance at light emitting diode 90.

Thus, FIG. 5 and FIG. 6 show that the circuit of FIG. 4 can thus be said to have three regions of operation. The first region is indicative of an analysis frequency well below the threshold frequency in which the light emitting diode is completely off. The second region is indicative of an analysis frequency nearly equal to but less than the threshold frequency in which the light emitting diode is partly on, at less than full brilliance. The third region is indicative of an analysis frequency equal to or exceeding the threshold frequency in which the light emitting diode is completely on at full brilliance.

Commercially available components plus the values for capacitors, inductors, and resistors, which can be utilized in the circuit illustrated are as follows:

TABLE

| Component | Description |
| --- | --- |
| Integrated Circuit 69 | Motorola Device MC 14031, Flip Flop |
| Inverters 62, 66, 68, 72, 76, 78 | Motorola Device MC 14049, Hex Buffer |
| Resistors 65, 75 | 100 kilohms, ¼ watts, 5% |
| Capacitors 67, 77 | 10 picofarads |
| Capacitors 61, 71 | 100 picofarads |
| Inductors 63, 73 | 47 microhenries |
| F/V Converter 28 | Analog Devices Model 453 |
| Integrated Circuit 112 | Motorola Device MC 14528, Monostable |
| Resistors 108, 109, 104 | 100 kilohms, ¼ watts, 5% |
| Resistors 102, 98 | 33 kilohms, ¼ watts, 5% |
| Resistor 113 | 1 kilohm, ¼ watts, 5% |
| Resistor 99 | 3.9 kilohms, ¼ watts, 5% |
| Resistor 105 | 698 ohms, ¼ watts, 5% |
| Capacitor 100 | 0.68 microfarads |
| Capacitor 106 | 0.1 microfarads |
| Capacitor 110 | 0.01 microfarads |
| Diode 113 | IN 914 |
| Diode 90 | Motorola Devices MV 5023, LED |
| Transistor 93 | Motorola Device 2N3904 |

Although the sensible signal according to the illustrated embodiment is a light emitting diode, it is apparent that other means for producing sensible signals, for example, an audio signal, can be used in accordance with the present invention.

As indicated, one aspect of the invention comprises means and method for calibrating a dielectric constant detector of a chromatographic analyzer. In calibrating the liquid chromatographic analyzer, carrier fluid is supplied to flow through both the reference and sample cells of the dielectric constant detector. The electrical capacitance of the two cells is balanced by adjusting the cell electrode spacing by adjustment, for example, of means 55 and 56 of FIG. 2. In the calibrate mode the comparator provides the operator a visual signal as to the closeness of cell balance. In practice the operator adjusts electrode spacing until the LED is extinguished thus indicating that the frequency difference between the first and second oscillator means is, in the illustrated embodiment, 187 Hz or less. If the nominal oscillator frequency of first and second oscillator means is, for example 100 kHz, the cells can be balanced, in the illustrated embodiment, to within 0.2%.

In the operate mode of the chromatographic analyzer the LED glows if the analysis frequency exceeds, for example, in the illustrated embodiment, 20 kHz, to provide the operator with a visual alarm status signal. In practice the most usual cause of the alarm signal is one of the cells of the dielectric constant detector becoming shorted.

The invention has been described in terms of a preferred embodiment as illustrated in FIGS. 1 through 6. As has been previously stated, many different configurations can be utilized and also many different electrical circuits can be utilized to process the output from the dielectric constant detector. In addition, variations which do not affect the operation of the dielectric constant detector are within the scope of the present invention. While the invention has been described in terms of a presently preferred embodiment, reasonable variations and modifications are possible by those skilled in the art within the scope of the described invention and the appended claims.

What is claimed is:

1. Apparatus comprising:

pulse generating means having an analysis frequency input, a timing circuit input, and a pulse output, and operable for producing an output pulse at the pulse output responsive to an edge of an input pulse at the analysis frequency input, said output pulse having a duration determined by a pulse width signal appearing at the timing cirucit input;

analysis frequency source means for producing an analysis frequency;

first means for electrically connecting the analysis frequency source means to the analysis frequency input of the pulse generating means;

timing circuit means for determining a threshold frequency and for producing a pulse width signal output responsive to an input pulse at the analysis frequency input;

second means for electrically connecting the timing circuit means output to the timing circuit input of the pulse generating means; and sensible signal means connected to the pulse output of the pulse generating means for producing a first sensible signal responsive to a condition that the analysis frequency is equal to or greater than the threshold frequency, for producing a second sensible signal responsive to a condition that the analysis frequency is approaching, but less than the threshold frequency, and for producing a third sensible signal reponsive to a condition that the analysis frequency is well below the threshold frequency.

2. Method for producing a sensible signal comprising:

generating an analysis frequency;

determining a threshold frequency by selecting an RC network, the RC time constant of the RC circuit being representative of the threshold frequency; generating a pulse at pulse intervals determined by the period of the analysis frequency;

charging a capacitor in the selected RC network responsive to a thus generated pulse, the time constant of the RC network determining the duration of the pulse;

producing a third sensible signal responsive to a condition that the analysis frequency is well below the threshold frequency;

producing a second sensible signal responsive to a condition that the analysis frequency is approaching, but less than, the threshold frequency; and producing a first sensible signal responsive to a condition that the analysis frequency is equal to or greater than the threshold frequency.

3. Apparatus comprising:

a voltage source;

pulse generating means comprising a monostable multivibrator having a timing circuit input, an analysis frequency input, and a pulse output, said pulse generating means being operable for producing an output pulse at the pulse output responsive to an edge of an input pulse at the analysis frequency input, said output pulse having a duration determined by a pulse width signal appearing at the timing circuit input;

analysis frequency source means for producing an analysis frequency;

first means for electrically connecting the analysis frequency source means to the analysis frequency input of the pulse generating means, said first means comprising an input network electrically connected to the analysis frequency input of the pulse generating means, said input network comprising a first input network resistor having a first lead electrically connected to the voltage source and a second lead electrically connected to the analysis frequency input of the pulse generating means, a second input network resistor having a first lead electrically connected to the analysis frequency input and a second lead electrically connected to ground, and an input network capacitor coupling analysis frequency to analysis frequency input of the pulse generating means;

timing circuit means for determining a threshold frequency and for producing a pulse with signal output responsive to an input pulse at the analysis frequency input, said timing circuit comprising a selectable RC network electrically connected to the timing circuit input of the multivibrator, the selectable RC network comprising a switch having a fixed terminal electrically connected to the timing circuit input and a plurality of selectable terminals, a capacitor having a first lead connected to the fixed terminal of the switch and a second lead electrically connected to ground, a plurality of resistors each having a respective first lead electrically connected to a selectable respective one of the plurality of selectable terminals of the switch and having a respective second lead electrically connected to a voltage source;

bias means electrically connected to the pulse output of the pulse generating means for producing a first bias signal responsive to a condition that the analysis frequency is greater than the threshold frequency, said bias means comprising an RC bias network electrically connected to the pulse output of the pulse generating means, the RC bias network comprising a diode having a cathode electrically connected to the pulse output and an anode, a bias capacitor having a first lead electrically connected to the anode of the diode and a second lead electrically connected to ground, a first bias resistor having a first lead electrically connected to the voltage source and a second lead electrically connected to the anode, a second bias resistor having a first lead electrically connected to the anode of the diode and a second lead, a third bias resistor having a first lead electrically connected to ground and a second lead, the second lead of the second bias resistor being electrically connected to the second lead of the third bias resistor;

second means for electrically connecting the timing circuit means output to the timing circuit input of the pulse generating means; and sensible signal means connected to the pulse output of the pulse generating means for producing a first sensible signal responsive to a condition that the analysis frequency is greater than the threshold frequency, said sensible signal means comprising an NPN transistor having an emitter electrically connected to ground, a base electrically connected to the second lead of the second bias resistor and to the second lead of the third bias resistor and a collector, a light emitting diode having a cathode electrically connected to the collector of the NPN transistor and an anode, and a load resistor having a first lead electrically connected to the anode of the light emitting diode and a second lead electrically connected to the voltage source.

* * * * *